(12) United States Patent
Guo et al.

(10) Patent No.: US 10,577,309 B2
(45) Date of Patent: Mar. 3, 2020

(54) METHOD FOR PREPARING PREGABALIN INTERMEDIATE 3-ISOBUTYLGLUTARIC ACID MONOAMIDE

(71) Applicants: ZHEJIANG HUAHAI PHARMACEUTICAL CO., LTD, Taizhou (CN); ZHEJIANG HUAHAI ZHICHENG PHARMACEUTICAL CO., LTD, Linhai (CN)

(72) Inventors: Pan Guo, Linhai (CN); Musong Liu, Linhai (CN); Zengle Zhou, Linhai (CN); Wenling Zhang, Linhai (CN); Peng Wang, Linhai (CN)

(73) Assignees: ZHEJIANG HUAHAI PHARMACEUTICALS CO., LTD, Taizhou (CN); ZHEJIANG HUAHAI ZHICHENG PHARMACEUTICAL CO., LTD, Linhai (CN)

( * ) Notice: Subject to any disclaimer, the term of this patent is extended or adjusted under 35 U.S.C. 154(b) by 0 days.

(21) Appl. No.: 16/313,262

(22) PCT Filed: Jun. 21, 2017

(86) PCT No.: PCT/CN2017/089317
§ 371 (c)(1),
(2) Date: Dec. 26, 2018

(87) PCT Pub. No.: WO2018/001148
PCT Pub. Date: Jan. 4, 2018

(65) Prior Publication Data
US 2019/0152894 A1 May 23, 2019

(30) Foreign Application Priority Data
Jun. 30, 2016 (CN) .......................... 2016 1 0529786

(51) Int. Cl.
*C07C 231/10* (2006.01)
*C07C 233/05* (2006.01)
*C07C 231/02* (2006.01)
*C07D 211/88* (2006.01)

(52) U.S. Cl.
CPC .......... *C07C 231/10* (2013.01); *C07C 231/02* (2013.01); *C07C 233/05* (2013.01); *C07D 211/88* (2013.01)

(58) Field of Classification Search
None
See application file for complete search history.

(56) References Cited

FOREIGN PATENT DOCUMENTS

| | | |
|---|---|---|
| CN | 105348123 | 2/1916 |
| CN | 105481708 | 4/1916 |
| CN | 106045873 A | 10/1916 |
| CN | 100410242 | 8/2008 |
| CN | 102898320 | 1/2013 |
| CN | 104140375 | 11/2014 |
| CN | 104496832 | 4/2015 |
| CN | 105152954 | 12/2015 |
| IN | 2010/CHE/3772 | 7/2012 |
| IN | 2012/MUM/2889 | 4/2014 |
| WO | WO 2011077463 A1 | 6/2011 |

OTHER PUBLICATIONS

International Search Report for PCT/CN2017/089317 dated Aug. 25, 2017.
Office Action issued in Corresponding Chinese Patent Application No. 201610529786, dated Nov. 19, 2019. (no English translation available).
Zhang et al., "Synthesis of Pregabalin," *Chinese Journal of Pharmaceuticals*, 2007, 38(9): 617-618.

*Primary Examiner* — Amy C Bonaparte
(74) *Attorney, Agent, or Firm* — Norton Rose Fulbright US LLP

(57) ABSTRACT

Provided is a method for preparing a pregabalin intermediate 3-isobutylglutaric acid monoamide. The method comprises: 1) adding 3-isobutylglutaric acid and urea into a first organic solvent; 2) keeping warm and refluxing when heated to 100-140° C.; 3) adding water when cooled to 70-90° C.; 4) adding an ion membrane alkaline when cooled to 40-60° C., adjusting the pH to 11.0-14.0, then keeping warm at 40-60° C.; 5) when finished keeping warm, removing an organic layer; 6) adding an acid into the water layer to adjust the pH to 1.0-3.0; 7) extracting the solution acquired in step 6) by using a second organic solvent of a total volume of V, vacuum distilling 0.5-0.6 V of the organic solvent from an organic layer acquired by extraction; and 8) cooling to 0-15° C. and crystallizing to acquire 3-isobutylglutaric acid monoamide.

9 Claims, No Drawings

METHOD FOR PREPARING PREGABALIN INTERMEDIATE 3-ISOBUTYLGLUTARIC ACID MONOAMIDE

The present application is a national phase application under 35 U.S.C. § 371 of International Application No. PCT/CN2017/089317 filed Jun. 21, 2017, which claims the benefit of priority of Chinese Patent Application No. 201610529786.5, titled "METHOD FOR PREPARING PREGABALIN INTERMEDIATE 3-ISOBUTYLGLU-TARIC ACID MONOAMIDE", filed on Jun. 30, 2016 before the China National Intellectual Property Administration. The entire contents of each of the above-referenced disclosures are incorporated herein by reference in their entireties.

FIELD OF THE INVENTION

The present invention provides a method for preparing a pregabalin intermediate 3-isobutylglutaric acid monoamide, belonging to the field of pharmaceutical and chemical industry.

BACKGROUND OF THE INVENTION

Pregabalin is a pharmacologically active S-isomer of 3-aminomethyl-5-methylhexanoic acid. It is a GABA (gamma-aminobutyric acid) receptor antagonist developed by Pfizer, USA, and has a dose-dependent protective effect on epileptic seizure. Specifically, pregabalin is an analog of the neurotransmitter GABA, which exerts anti-epileptic effect by inhibiting the a2-subunit of the CNS voltage-dependent calcium channel, and has good lipid solubility to pass through the blood-brain barrier, showing better anti-epilepsy treatment effect in clinical trials.

Pregabalin first came into the market of UK in 2004. It was clinically used to treat neuropathic pain caused by diabetes, post-herpetic neuralgia, and adjuvant treatment of localized incomplete seizures in adult patients. It is the first drug approved by the FDA for the treatment of more than 2 types of neuropathic pain. The drug is administered less frequently and thus with less adverse reactions. In March 2006, indications were added for treating generalized anxiety disorder and social anxiety disorder. In June 2007, pregabalin was approved by the FDA as the first drug to treat fibromyalgia syndrome. In 2009, it was approved additionally for the treatment of spinal cord injury, trauma, multiple sclerosis, diabetic neuropathic pain and herpes zoster neuropathic pain.

Pregabalin is considered to be the most promising drug in epilepsy treatment because of its good anti-anxiety effect, good therapeutic effect on neuralgia and epilepsy, and convenient administration. 3-Isobutylglutaric acid monoamide is a very important intermediate in the chemical synthesis process of pregabalin.

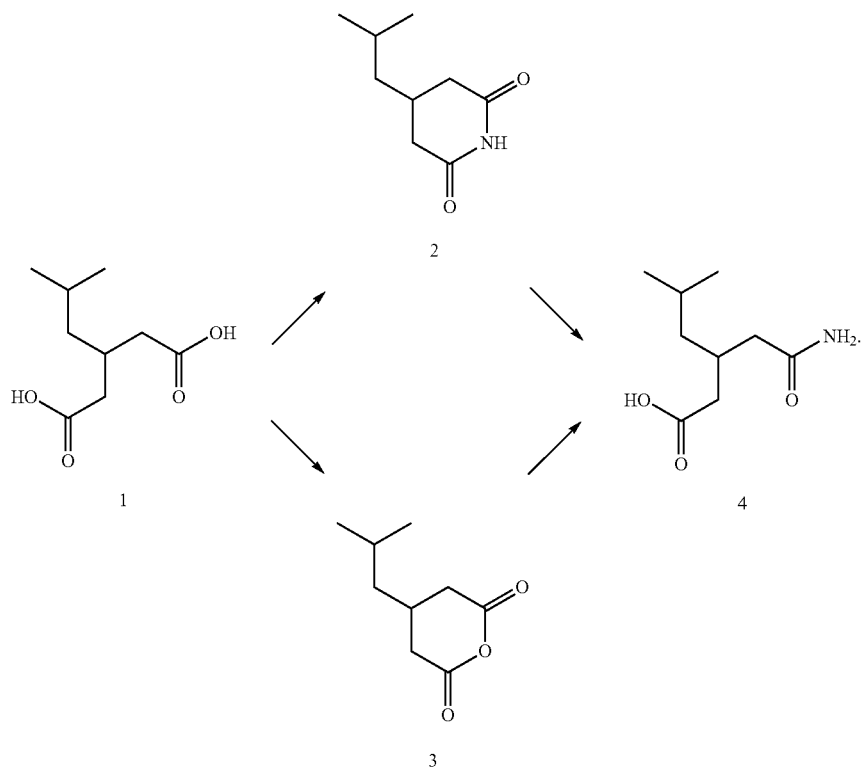

Reaction scheme 1

The preparation of the pregabalin intermediate (3-isobutylglutaric acid monoamide) from 3-isobutylglutaric acid reported in the literature is basically carried out according to the two synthetic routes in the above reaction scheme 1. Wherein, in the first route (i.e., the route of Compound 1-Compound 2-Compound 4), when preparing compound 2, a high-temperature solvent-free reaction is employed, and then ring-opening reaction is performed on compound 2 to obtain 3-isobutylglutaric acid monoamide. The disadvantage of the process is that in the solvent-free reaction, the viscosity of the reaction system is so large that the stirring resistance is large, and the safety hazard is easy to occur; the process belongs to the solid-liquid reaction, and the urea as one of the reactants in the reaction process is easily crystallized on the reactor wall, which easily causes clogging of the distillation outlet and the exhaust gas line, thereby increasing the difficulty of cleaning, and also resulting in low urea utilization rate, incomplete reaction, low yield, and total yield of the two-step reaction is only about 60%-70%.

SUMMARY OF THE INVENTION

The object of the present invention is to provide a method for preparing a pregabalin intermediate 3-isobutylglutaric acid monoamide, which is safe and easy to operate while the yield of product is relatively high.

The method for preparing a pregabalin intermediate 3-isobutylglutaric acid monoamide provided by the present invention comprises:

1) adding 3-isobutylglutaric acid and urea to a first organic solvent;

2) heating to a temperature of 100-140° C., and refluxing while maintaining the temperature;

3) cooling a mixture obtained in step 2) to 70-90° C., then adding water;

4) cooling a mixture obtained in step 3) to 40-60° C., adding ion-exchange membrane caustic soda solution to adjust the pH value to 11.0-14.0, while maintaining the temperature of 40-60° C.;

5) separating an organic layer after maintaining the temperature;

6) adding an acid into an aqueous layer to adjust the pH value to 1.0-3.0;

7) extracting the solution obtained in step 6) with a second organic solvent of a total volume of V, distilling an organic layer obtained by extraction under reduced pressure to remove 0.5-0.6 V of organic solvent; and 8) cooling to 0-15° C. and crystallizing to obtain 3-isobutylglutaric acid monoamide, preferably performing centrifuging, filtering and drying after crystallization.

The reaction formula involved in the above method of the present invention is as follows:

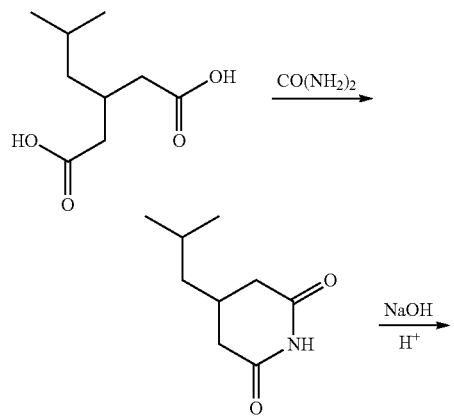

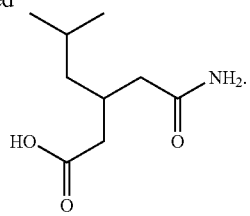

In the above method, the first organic solvent in the step 1) can be an aprotic organic solvent, for example, selected from the group consisting of toluene, xylene, and octane. The xylene may be o-xylene, m-xylene and p-xylene or any mixtures thereof. In step 1), the ratio of the volume of the first organic solvent in milliliters to the mass of 3-isobutylglutaric acid in grams may be 2:1 to 6:1; the mass ratio of urea to 3-isobutylglutaric acid may be 0.2:1 to 0.6:1.

The duration of refluxing and maintaining temperature in step 2) may be 2.0 h to 5.0 h.

The mass of water added in step 3) may be 1.5 to 4.0 times as much as 3-isobutylglutaric acid.

The duration of maintaining temperature in step 4) may be 0.5 h to 4.0 h. The ion-exchange membrane caustic soda solution used in step 4) is an aqueous sodium hydroxide solution prepared by electrolyzing saline solution with ion exchange membrane method.

The second organic solvent in step 7) may be an aprotic organic solvent, for example, selected from the group consisting of ethyl acetate, dichloromethane and toluene.

The duration of crystallization in step 8) may be 1.0 h to 6.0 h. After crystallization in step 8), centrifuging, filtering and drying can be carried out.

The method of the present invention has following obvious advantages in terms of safety and environmental protection, quality and efficiency improvement in view of fierce competition in the market:

1. The method of the present invention can prepare compound 4 directly without separating compound 2 from the reaction system during the reaction, which simplifies the reaction step;

2. The method of the present invention is a liquid-liquid reaction system, thereby eliminating the crystallization phenomenon of urea, preventing the clogging of the distillation outlet and the exhaust gas pipeline, and reducing the difficulty of cleaning the reaction vessels;

3. The method of the present invention also reduces the reaction temperature, allows mild reaction conditions, increases the utilization rate of urea, increases the degree of reaction, and significantly improves the yield and productivity to a certain extent.

DETAILED DESCRIPTION OF THE INVENTION

The method of the present invention is exemplified below in conjunction with the examples, but these examples are not intended to limit the present invention in any way.

Example 1

100 g of 3-isobutylglutaric acid, 400 mL of toluene and 40 g of urea were added into a four-neck flask, and the mixture was stirred and heated to 110° C. After the end of temperature rise, the mixture was stirred under reflux for 3 hours while maintaining the temperature. After cooling to 80° C., 200 mL of water was added to the mixture. The mixture was further cooled to 40° C., and the pH value was adjusted to 13 with ion-exchange membrane caustic soda solution. The mixture was stirred while maintaining at 40° C. for 1 h, and the organic layer was separated. Hydrochloric acid was added dropwise to adjust the pH of aqueous layer to 1.0, and the aqueous layer was extracted twice with ethyl acetate (350 mL+150 mL). The ethyl acetate layers were combined and 280 mL of ethyl acetate was distilled off under reduced pressure. The mixture was cooled to 5° C. and crystallized for 2 h while maintaining the temperature, and then filtered by suction and dried to obtain 3-isobutylglutaric acid monoamide, weight: 91.5 g, yield: 92.0%, purity 99.1%.

Example 2

100 g of 3-isobutylglutaric acid, 400 mL of xylene and 40 g of urea were added into a four-neck flask, and the mixture was stirred and heated to 130° C. After the end of temperature rise, the mixture was stirred under reflux for 3 hours while maintaining the temperature. After cooling to 80° C., 200 mL of water was added to the mixture. The mixture was further cooled to 40° C., and the pH value was adjusted to 12 with ion-exchange membrane caustic soda solution. The mixture was stirred while maintaining at 40° C. for 1 h, and the organic layer was separated. Hydrochloric acid was added dropwise to adjust the pH of aqueous layer to 1.0, and the aqueous layer was extracted twice with ethyl acetate (350 mL+150 mL). The ethyl acetate layers were combined and 280 mL of ethyl acetate was distilled off under reduced pressure. The mixture was cooled to 5° C. and crystallized for 1 h while maintaining the temperature, and then filtered by suction and dried to obtain 3-isobutylglutaric acid monoamide, weight: 93.0 g, yield: 93.5%, purity 98.8%.

Example 3

100 g of 3-isobutylglutaric acid, 400 mL of octane and 40 g of urea were added into a four-neck flask, and the mixture was stirred and heated to 120° C. After the end of temperature rise, the mixture was stirred under reflux for 2 hours while maintaining the temperature. After cooling to 90° C., 300 mL of water was added to the mixture. The mixture was further cooled to 50° C., and the pH value was adjusted to 13 with ion-exchange membrane caustic soda solution. The mixture was stirred while maintaining at 50° C. for 2 h, and the organic layer was separated. Hydrochloric acid was added dropwise to adjust the pH of aqueous layer to 2.0, and the aqueous layer was extracted twice with ethyl acetate (350 mL+150 mL). The ethyl acetate layers were combined and 260 mL of ethyl acetate was distilled off under reduced pressure. The mixture was cooled to 10° C. and crystallized for 2 h while maintaining the temperature, and then filtered by suction and dried to obtain 3-isobutylglutaric acid monoamide, weight: 91.7 g, yield: 92.2%, purity 99.3%.

Example 4

100 g of 3-isobutylglutaric acid, 600 mL of toluene, and 30 g of urea were added into a four-neck flask, and the mixture was stirred and heated to 100° C. After the end of temperature rise, the mixture was stirred under reflux for 4 hours while maintaining the temperature. After cooling to 90° C., 150 mL of water was added to the mixture. The mixture was further cooled to 60° C., and the pH value was adjusted to 12 with ion-exchange membrane caustic soda solution. The mixture was stirred while maintaining at 60° C. for 3 h, and the organic layer was separated. Hydrochloric acid was added dropwise to adjust the pH of aqueous layer to 2.0, and the aqueous layer was extracted twice with dichloromethane (350 mL+150 mL). The dichloromethane layers were combined and 280 mL of dichloromethane was distilled off under reduced pressure. The mixture was cooled to 5° C. and crystallized for 2 h while maintaining the temperature, and then filtered by suction and dried to obtain 3-isobutylglutaric acid monoamide, weight: 89.0 g, yield: 89.5%, purity 98.6%.

Example 5

100 g of 3-isobutylglutaric acid, 300 mL of octane and 50 g of urea were added into a four-neck flask, and the mixture was stirred and heated to 125° C. After the end of temperature rise, the mixture was stirred under reflux for 5 hours while maintaining the temperature. After cooling to 80° C., 300 mL of water was added to the mixture. The mixture was further cooled to 60° C., and the pH value was adjusted to 13 with ion-exchange membrane caustic soda solution. The mixture was stirred while maintaining at 60° C. for 1 h, and the organic layer was separated. Hydrochloric acid was added dropwise to adjust the pH of aqueous layer to 3.0, and the aqueous layer was extracted twice with toluene (350 mL+150 mL). The toluene layers were combined and 280 mL of toluene was distilled off under reduced pressure. The mixture was cooled to 5° C. and crystallized for 1 h while maintaining the temperature, and then filtered by suction and dried to obtain 3-isobutylglutaric acid monoamide, weight: 89.0 g, yield: 89.5%, purity 99.1%.

Example 6

100 g of 3-isobutylglutaric acid, 500 mL of xylene and 40 g of urea were added into a four-neck flask, and the mixture was stirred and heated to 130° C. After the end of temperature rise, the mixture was stirred under reflux for 5 hours while maintaining the temperature. After cooling to 80° C., 300 mL of water was added to the mixture. The mixture was further cooled to 40° C., and the pH value was adjusted to 13 with ion-exchange membrane caustic soda solution. The mixture was stirred while maintaining at 40° C. for 3 h, and the organic layer was separated. Hydrochloric acid was added dropwise to adjust the pH of aqueous layer to 2.0, and the aqueous layer was extracted twice with ethyl acetate (350 mL+150 mL). The ethyl acetate layers were combined and 280 mL of ethyl acetate was distilled off under reduced pressure. The mixture was cooled to 5° C. and crystallized for 1 h while maintaining the temperature, and then filtered by suction and dried to obtain 3-isobutylglutaric acid monoamide, weight: 89.5 g, yield: 90.0%, purity 99.5%.

Example 7

100 g of 3-isobutylglutaric acid, 500 mL of xylene and 55 g of urea were added into a four-neck flask, and the mixture was stirred and heated to 130° C. After the end of temperature rise, the mixture was stirred under reflux for 3 hours while maintaining the temperature. After cooling to 70° C., 300 mL of water was added to the mixture. The mixture was further cooled to 55° C., and the pH value was adjusted to 13 with ion-exchange membrane caustic soda solution. The mixture was stirred while maintaining at 55° C. for 1 h, and the organic layer was separated. Hydrochloric acid was added dropwise to adjust the pH of aqueous layer to 2.0, and the aqueous layer was extracted twice with dichloromethane (350 mL+150 mL). The dichloromethane layers were combined and 300 mL of dichloromethane was distilled off under reduced pressure. The mixture was cooled to 5° C. and crystallized for 1 h while maintaining the temperature, and then filtered by suction and dried to obtain 3-isobutylglutaric acid monoamide, weight: 93.0 g, yield: 93.5%, purity 99.0%.

Example 8

100 g of 3-isobutylglutaric acid, 450 mL of toluene and 60 g of urea were added into a four-neck flask, and the mixture was stirred and heated to 115° C. After the end of temperature rise, the mixture was stirred under reflux for 2 hours while maintaining the temperature. After cooling to 90° C., 200 mL of water was added to the mixture. The mixture was further cooled to 45° C., and the pH value was adjusted to 12 with ion-exchange membrane caustic soda solution. The mixture was stirred while maintaining at 45° C. for 3 h, and the organic layer was separated. Hydrochloric acid was added dropwise to adjust the pH of aqueous layer to 2.0, and the aqueous layer was extracted twice with toluene (350 mL+150 mL). The toluene layers were combined and 250 mL of toluene was distilled off under reduced pressure. The mixture was cooled to 10° C. and crystallized for 2 h while maintaining the temperature, and then filtered by suction and dried to obtain 3-isobutylglutaric acid monoamide, weight: 91.8 g, yield: 92.3%, purity 99.2%.

Example 9

100 g of 3-isobutylglutaric acid, 350 mL of toluene and 40 g of urea were added into a four-neck flask, and the mixture was stirred and heated to 115° C. After the end of temperature rise, the mixture was stirred under reflux for 3 hours while maintaining the temperature. After cooling to 90° C., 300 mL of water was added to the mixture. The mixture was further cooled to 50° C., and the pH value was adjusted to 14 with ion-exchange membrane caustic soda solution. The mixture was stirred while maintaining at 50° C. for 4 h, and the organic layer was separated. Hydrochloric acid was added dropwise to adjust the pH of aqueous layer to 2.0, and the aqueous layer was extracted twice with ethyl acetate (350 mL+150 mL). The ethyl acetate layers were combined and 300 mL of ethyl acetate was distilled off under reduced pressure. The mixture was cooled to 10° C. and crystallized for 2 h while maintaining the temperature, and then filtered by suction and dried to obtain 3-isobutylglutaric acid monoamide, weight: 90.6 g, yield: 91.1%, purity 99.2%.

Example 10

100 g of 3-isobutylglutaric acid, 300 mL of xylene and 50 g of urea were added into a four-neck flask, and the mixture was stirred and heated to 135° C. After the end of temperature rise, the mixture was stirred under reflux for 3 hours while maintaining the temperature. After cooling to 80° C., 300 mL of water was added to the mixture. The mixture was further cooled to 40° C., and the pH value was adjusted to 13 with ion-exchange membrane caustic soda solution. The mixture was stirred while maintaining at 40° C. for 2 h, and the organic layer was separated. Hydrochloric acid was added dropwise to adjust the pH of aqueous layer to 2.0, and the aqueous layer was extracted twice with ethyl acetate (350 mL+150 mL). The ethyl acetate layers were combined and 270 mL of ethyl acetate was distilled off under reduced pressure. The mixture was cooled to 10° C. and crystallized for 0.5 h while maintaining the temperature, and then filtered by suction and dried to obtain 3-isobutylglutaric acid monoamide, weight: 92.4 g, yield: 92.9%, purity 99.1%.

Example 11

100 g of 3-isobutylglutaric acid, 600 mL of octane and 50 g of urea were added into a four-neck flask, and the mixture was stirred and heated to 125° C. After the end of temperature rise, the mixture was stirred under reflux for 4 hours while maintaining the temperature. After cooling to 80° C., 150 mL of water was added to the mixture. The mixture was further cooled to 40° C., and the pH value was adjusted to 13 with ion-exchange membrane caustic soda solution. The mixture was stirred while maintaining at 40° C. for 1 h, and the organic layer was separated. Hydrochloric acid was added dropwise to adjust the pH of aqueous layer to 1.0, and the aqueous layer was extracted twice with dichloromethane (350 mL+150 mL). The dichloromethane layers were combined and 270 mL of dichloromethane was distilled off under reduced pressure. The mixture was cooled to 5° C. and crystallized for 1 h while maintaining the temperature, and then filtered by suction and dried to obtain 3-isobutylglutaric acid monoamide, weight: 92.8 g, yield: 93.3%, purity 98.8%.

Example 12

100 g of 3-isobutylglutaric acid, 300 mL of xylene and 20 g of urea were added into a four-neck flask, and the mixture was stirred and heated to 130° C. After the end of temperature rise, the mixture was stirred under reflux for 2 hours while maintaining the temperature. After cooling to 70° C., 200 mL of water was added to the mixture. The mixture was further cooled to 50° C., and the pH value was adjusted to 12 with ion-exchange membrane caustic soda solution. The mixture was stirred while maintaining at 50° C. for 2 h, and the organic layer was separated. Hydrochloric acid was added dropwise to adjust the pH of aqueous layer to 2.0, and the aqueous layer was extracted twice with ethyl acetate (350 mL+150 mL). The ethyl acetate layers were combined and 250 mL of ethyl acetate was distilled off under reduced pressure. The mixture was cooled to 0° C., and crystallized for 1 h while maintaining the temperature, and then filtered by suction and dried to obtain 3-isobutylglutaric acid monoamide, weight: 88.4 g, yield: 88.9%, purity 99.3%.

Comparative Example 1

This comparative example uses the route of compound 1-compound 2-compound 4 in the reaction scheme 1 to prepare 3-isobutylglutaric acid monoamide, and the specific process conditions are as follows: 100 g of 3-isobutylglutaric acid and 20 g of urea were added into a four-neck flask, and the mixture was stirred and heated to 130° C. After the end of temperature rise, the mixture was stirred while maintaining the temperature for 2 h. After cooling to 70° C., 200 mL of water was added to the mixture. The mixture was further cooled to 50° C., and the pH value was adjusted to 12 with ion-exchange membrane caustic soda solution. The mixture was stirred while maintaining at 50° C. for 2 h, and hydrochloric acid was added dropwise to adjust the pH of mixture to 2.0. The aqueous layer was extracted twice with ethyl acetate (350 mL+150 mL). The ethyl acetate layers were combined and 250 mL of ethyl acetate was distilled off under reduced pressure. The mixture was cooled to 0° C. and crystallized for 1 h while maintaining the temperature, and then filtered by suction and dried to obtain 3-isobutylglutaric acid monoamide. The weight of the obtained product was 64.7 g, and the total yield of the two-step reaction was 65.0%, and the purity was 98.2%.

As can be seen from the above Examples 1-12 and Comparative Example 1, the method provided by the present invention can obtain a higher yield than the conventional synthesis method. At the same time, the method of the present invention can prepare compound 4 directly without separating compound 2 from the reaction system during the reaction, which simplifies the reaction step. The method of the invention is a liquid-liquid reaction system, thereby eliminating the crystallization phenomenon of urea, preventing the clogging of the distillation outlet and the exhaust gas pipeline, reducing the difficulty of cleaning the reaction vessels; lowering the reaction temperature and allowing mild reaction conditions to a certain extent. In summary, the method for preparing the pregabalin intermediate 3-isobutylglutaric acid monoamide provided by the present invention is safe, environmental-friendly, simple and convenient, and has high yield.

The invention claimed is:

1. A method for preparing a pregabalin intermediate 3-isobutylglutaric acid monoamide, comprising:
   1) adding 3-isobutylglutaric acid and urea to a first organic solvent;
   2) heating to a temperature of 100-140° C., and refluxing while maintaining the temperature;
   3) cooling the mixture obtained in step 2) to 70-90° C., then adding water;
   4) cooling the mixture obtained in step 3) to a temperature of 40-60° C., then adding an ion-exchange membrane caustic soda solution to adjust the pH value of the mixture to 11.0-14.0, while maintaining the temperature of 40-60° C.;
   5) separating an organic layer after maintaining the temperature;
   6) adding an acid into the aqueous layer to adjust the pH value of the aqueous layer to 1.0-3.0;
   7) extracting the aqueous solution obtained in step 6) with a second organic solvent of a total volume of V, distilling the second organic layer obtained by extraction under reduced pressure to remove 0.5V-0.6 V of the second organic solvent; and
   8) cooling the distilled second organic layer to 0-15° C. and crystallizing to obtain 3-isobutylglutaric acid monoamide.

2. The method according to claim 1, wherein the ratio of the volume of the first organic solvent in step 1) in milliliters to the mass of 3-isobutylglutaric acid in grams is 2:1 to 6:1; and the mass ratio of urea to 3-isobutylglutaric acid is 0.2:1 to 0.6:1.

3. The method according to claim 1, wherein the first organic solvent in step 1) is selected from the group consisting of toluene, xylene and octane.

4. The method according to claim 1, wherein the duration of refluxing and maintaining the temperature in step 2) is 2.0 h to 5.0 h.

5. The method according to claim 1, wherein the mass of water added in step 3) is 1.5 to 4.0 times as much as the mass of 3-isobutylglutaric acid.

6. The method according to claim 1, wherein step 4) further comprises stirring and maintaining the temperature of the mixture at 40-60° C. for 0.5 h to 4.0 h.

7. The method according to claim 1, wherein the second organic solvent in step 7) is selected from the group consisting of ethyl acetate, dichloromethane and toluene.

8. The method according to claim 1, wherein the duration of crystallizing in step 8) is 1.0 h to 6.0 h.

9. The method according to claim 1, further comprising centrifuging, filtering and drying the 3-isobutylglutaric acid monoamide after crystallizing in step 8).

* * * * *

UNITED STATES PATENT AND TRADEMARK OFFICE
CERTIFICATE OF CORRECTION

PATENT NO. : 10,577,309 B2
APPLICATION NO. : 16/313262
DATED : March 3, 2020
INVENTOR(S) : Pan Guo et al.

Page 1 of 1

It is certified that error appears in the above-identified patent and that said Letters Patent is hereby corrected as shown below:

On the Title Page

Item (73), Assignees, Line 2:
Delete "PHARMACEUTICALS" and replace with -- PHARMACEUTICAL --.

Signed and Sealed this
Eighteenth Day of August, 2020

Andrei Iancu
*Director of the United States Patent and Trademark Office*